US012636236B2

(12) United States Patent
Ito et al.

(10) Patent No.: US 12,636,236 B2
(45) Date of Patent: May 26, 2026

(54) FILM-FORMING COMPOSITION FOR SKIN

(71) Applicant: KAO CORPORATION, Tokyo (JP)

(72) Inventors: Motoaki Ito, Sumida-ku (JP); Kaori Ishida, Sumida-ku (JP)

(73) Assignee: KAO CORPORATION, Tokyo (JP)

(*) Notice: Subject to any disclaimer, the term of this patent is extended or adjusted under 35 U.S.C. 154(b) by 393 days.

(21) Appl. No.: 18/254,895

(22) PCT Filed: Nov. 24, 2021

(86) PCT No.: PCT/JP2021/043013
§ 371 (c)(1),
(2) Date: May 30, 2023

(87) PCT Pub. No.: WO2022/114008
PCT Pub. Date: Jun. 2, 2022

(65) Prior Publication Data

US 2024/0009088 A1 Jan. 11, 2024

(30) Foreign Application Priority Data

Nov. 30, 2020 (JP) ................................. 2020-199007

(51) Int. Cl.

| | |
|---|---|
| ***A61K 8/81*** | (2006.01) |
| ***A61G 19/00*** | (2006.01) |
| ***A61K 8/02*** | (2006.01) |
| ***A61K 8/85*** | (2006.01) |
| ***A61K 8/87*** | (2006.01) |
| ***A61K 8/891*** | (2006.01) |
| ***A61K 8/895*** | (2006.01) |
| ***A61Q 19/00*** | (2006.01) |

(52) U.S. Cl.
CPC .............. *A61K 8/027* (2013.01); *A61G 19/00* (2013.01); *A61K 8/891* (2013.01); *A61K 2800/412* (2013.01)

(58) Field of Classification Search
None
See application file for complete search history.

(56) References Cited

U.S. PATENT DOCUMENTS

| | | | | |
|---|---|---|---|---|
| 2002/0142014 | A1 | 10/2002 | Afriat et al. | |
| 2002/0182238 | A1 | 12/2002 | Creton | |
| 2002/0197289 | A1 | 12/2002 | Chevalier et al. | |
| 2006/0057085 | A1 | 3/2006 | Lezer | |
| 2007/0196401 | A1 | 8/2007 | Naruse et al. | |
| 2021/0393502 | A1* | 12/2021 | Sano | A61K 8/73 |

FOREIGN PATENT DOCUMENTS

| | | | | |
|---|---|---|---|---|
| EP | 1 550 430 | A2 | 7/2005 | |
| EP | 3 903 886 | A1 | 11/2021 | |
| EP | 3 943 200 | A1 | 1/2022 | |
| JP | 2001-64153 | A | 3/2001 | |
| JP | 2002-154932 | A | 5/2002 | |
| JP | 2002-193746 | A | 7/2002 | |
| JP | 2002-293718 | A | 10/2002 | |
| JP | 2002-293731 | A | 10/2002 | |
| JP | 2005-320506 | A | 11/2005 | |
| JP | 2008-115120 | A | 5/2008 | |
| JP | 2020-105119 | A | 7/2020 | |
| WO | WO-2020138144 | A1 * | 7/2020 | A61K 8/731 |
| WO | WO 2020/194911 | A1 | 10/2020 | |

OTHER PUBLICATIONS

International Search Report mailed on Feb. 1, 2022 in PCT/JP2021/043013 filed on Nov. 24, 2021 (2 pages).
Anonymous, “Technical Data Sheet KSG-16 Silicone Elastomer”. Shin-Etsu Chemical Co., Ltd., Nov. 7, 2017, pp. 1-2, XP093203985.
Extended European Search Report issued Oct. 11, 2024 in European Patent Application No. 21897980.5, 10 pages.

* cited by examiner

*Primary Examiner* — Brian Gulledge
(74) *Attorney, Agent, or Firm* — Oblon, McClelland, Maier & Neustadt, L.L.P.

(57) ABSTRACT

A film-forming composition for skin, including components (A) and (B): (A) a silicone-based film-forming agent; and (B) a fiber having an average fiber diameter of 0.1 μm or more and 7 μm or less in an amount of 0.05 mass % or more and 2 mass % or less relative to the whole film-forming composition. A mass ratio of the component (B) to the component (A), (B/A), is 0.05 or more and 1 or less.

18 Claims, 1 Drawing Sheet

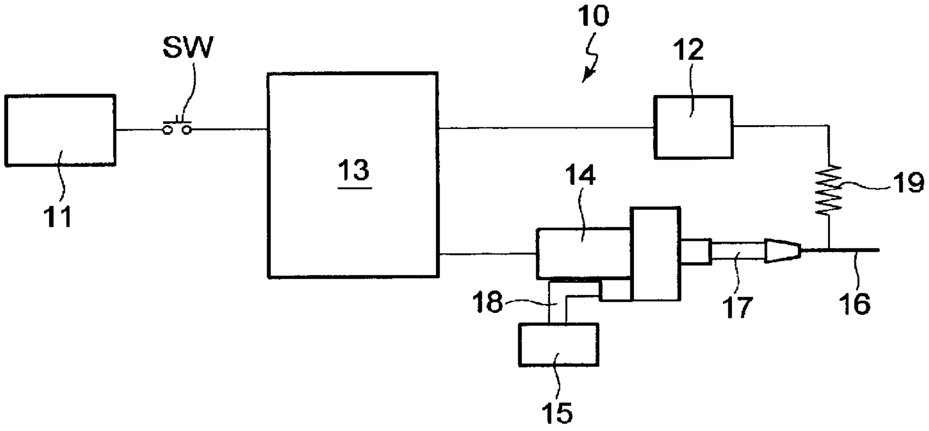
10
SW
12
11
13
14
19
18
17
16
15

FILM-FORMING COMPOSITION FOR SKIN

CROSS REFERENCE TO RELATED APPLICATIONS

This application is a National Stage entry under 35 U.S.C. § 371 of PCT/JP2021/043013, filed on Nov. 24, 2021, and claims priority to Japanese Patent Application No. 2020-199007, filed on Nov. 30, 2020. The entire contents of both are incorporated herein by reference.

FIELD OF THE INVENTION

The present invention relates to a film-forming composition for skin that can form a favorable cosmetic film on a skin surface.

BACKGROUND OF THE INVENTION

Techniques for incorporating fibers into cosmetics are well known and are broadly adopted for mascara and so on. In order to make up a keratinous substance, such as skin, a composition containing a fiber and a copolymer including a carboxylate group and a polydimethylsiloxane group in a physiologically acceptable medium (Patent Literature 1) has been reported. A technique of incorporating a fiber in a cosmetic for reducing the irritation of a cosmetic including an irritative component (Patent Literature 2) and a cosmetic including a fiber and an anti-aging agent for camouflaging skin imperfections and treating signs of skin aging (Patent Literature 3) have been also reported. Furthermore, it has been reported to blend a fiber dispersion with a monofilament diameter of 1 to 500 nm and the sum Pa of the monofilament ratio of 60% or more, in order to obtain a blended solution, emulsion, or gel excellent in uniform dispersibility and long-term dispersion stability (Patent Literature 4). Furthermore, a cosmetic containing a short fiber obtained by cutting an extra-superfine synthetic fiber having a diameter of about 2 μm into a length of 5 to 50 μm has been reported (Patent Literature 5).

Patent Literature 1: JP-A-2002-193746

Patent Literature 2: JP-A-2002-293718

Patent Literature 3: JP-A-2002-293731

Patent Literature 4: JP-A-2005-320506

Patent Literature 5: JP-A-2001-64153

SUMMARY OF THE INVENTION

The present invention relates to a film-forming composition for skin, comprising the following components (A) and (B):

(A) a silicone-based film-forming agent; and (B) a fiber having an average fiber diameter of 0.1 μm or more and 7 μm or less in an amount of 0.05 mass % or more and 2 mass % or less relative to the whole film-forming composition, wherein the mass ratio of the component (B) to the component (A), (B/A), is 0.05 or more and 1 or less.

The present invention relates to a method for producing a film on a skin surface, comprising applying the film-forming composition for skin to the skin.

Furthermore, the present invention relates to a film comprising the film-forming composition for skin.

BRIEF DESCRIPTION OF DRAWING

FIG. 1 is a schematic diagram showing a structure of the electrostatic spraying device used for forming a fiber of a component (B).

DETAILED DESCRIPTION OF THE INVENTION

Since the fiber diameters adopted in Patent Literatures 1 to 3 are large, i.e., 0.9 dtex (=10.7 μm), no network is formed by the fiber, and thus it causes a problem in the durability of cosmetic films. Since the fiber used in Patent Literature 4 has a long fiber length, the aspect ratio is significantly large, and a film having high durability may not be formed. Further, the cosmetic disclosed in Patent Literature 5 cannot form a stable film on skin.

According to studies by the present inventors, it was found that films obtained by the cosmetics disclosed in Patent Literatures 1 to 5 are vulnerable to physical rubbing, and there is a problem with scratch resistance.

Therefore, the present invention provides a film-forming composition for skin that can form a stable film on skin, and the obtained film has excellent scratch resistance.

The present inventors conducted various studies to solve the above problems. As a result, they found that a film-forming composition for skin prepared by blending a super fine and short fiber having a predetermined fiber diameter and a silicone-based film-forming agent at a predetermined ratio can form a stable film on skin, and the obtained film has significantly improved scratch resistance and when used as a cosmetic film, the covering power of the cosmetic film is improved.

According to the film-forming composition for skin of the present invention, a stable film can be formed on skin, and the scratch resistance of the obtained film is significantly improved. When the film is used as a cosmetic film, the covering power of the cosmetic film is improved, and a bright color excellent in color development can be achieved.

The film-forming composition for skin of the present invention contains the following components (A) and (B):

(A) a silicone-based film-forming agent; and (B) a fiber having an average fiber diameter of 0.1 μm or more and 7 μm or less in an amount of 0.05 mass % or more and 2 mass % or less relative to the whole film-forming composition, in which the mass ratio of the component (B) to the component (A), (B/A), is 0.05 or more and 1 or less.

The silicone-based film-forming agent of the component (A) is a component having a silicone structure and can form a film on skin when applied to the skin. Specifically, the silicone-based film-forming agent is dispersed or dissolved in the film-forming composition. The silicone-based film-forming agent is preferably dispersed or dissolved in an oil component.

In the present invention, the term "silicone structure" refers to a structure represented by the following formula (I):

(I)

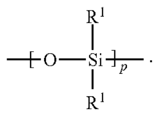

In the formula (I), $R^1$s each independently represent a hydrocarbon group having from 1 to 12 carbon atoms; and p is an integer of 1 or more. From the viewpoint of forming a film with high scratch resistance on skin (hereinafter, also referred to as "from the viewpoint of forming a film excellent in scratch resistance") by application to the skin and from the viewpoint of versatility, $R^1$ is preferably an alkyl group having from 1 to 12 carbon atoms or an aryl group having from 6 to 12 carbon atoms, more preferably an alkyl group having from 1 to 12 carbon atoms or a phenyl group, further preferably an alkyl group having from 1 to 3 carbon atoms, and even more preferably a methyl group.

The silicone-based film-forming agent of the component (A) is preferably a polymer having a silicone structure in part and may have not only a D-unit ($R^1{}_2SiO_{2/2}$) structure but also an M-unit ($R^1{}_3SiO_{1/2}$) structure, a T-unit ($R^1SiO_{3/2}$) structure, and a Q-unit ($SiO_{4/2}$) structure.

In a polymer having a silicone structure in part, the silicone structure may be present in either the main chain or the side chain of the polymer and is preferably present in the side chain.

When the silicone structure is present in the polymer main chain, the binding form is also not particularly limited. For example, the silicone structure may be present at a terminal of the polymer main chain. Alternatively, the polymer may be a copolymerization polymer in which the silicone structure is bound to the polymer main chain in a block form or a random form.

A polymer graft-modified by a compound having a silicone structure can also be used.

As a specific example of the component (A), one or two or more selected from the group consisting of silicone-modified pullulan, a silicone structure-containing silicic acid compound, and silicone dendrimer.

Examples of the silicone-modified pullulan include pullulan having a silicone structure in the side chain. Specifically, from the viewpoint of forming a film excellent in scratch resistance and the viewpoint of versatility, preferred is silicone-modified pullulan in which at least a part of hydrogen atoms of OH groups in the pullulan is substituted with a group represented by the following formula (1):

$$—Z^1—SiX_aR^2{}_{3-a} \quad (1).$$

In the formula, $Z^1$ is a single bond or a divalent organic group; $R^2$ is each independently an alkyl group having from 1 to 12 carbon atoms; X is a group represented by the following formula (i); and a is an integer of 1 or more and 3 or less.

(i)

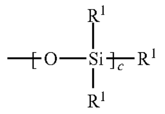

In the formula, $R^1$ is the same as above; and c is an integer of 1 or more and 5 or less.

From the viewpoint of forming a film excellent in scratch resistance and the viewpoint of versatility, X is preferably a trimethylsiloxane group, and a is preferably 3.

In the formula (1), from the viewpoint of forming a film excellent in scratch resistance and the viewpoint of versatility, $Z^1$ is preferably a divalent organic group, more preferably a divalent group represented by the following formula (2) or (3), and more preferably a divalent group represented by the following formula (3):

(2)

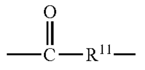

(3)

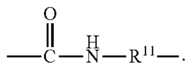

In the formulae, $R^{11}$ is an alkylene group having from 1 to 10 carbon atoms, and examples thereof include a methylene group, an ethylene group, a trimethylene group, a propylene group, and a butylene group. Among them, from the viewpoint of forming a film excellent in scratch resistance and the viewpoint of versatility, preferred are an ethylene group, a trimethylene group, and a propylene group, and more preferred are a trimethylene group and a propylene group.

Examples of commercially available silicone-modified pullulan include "TSPL-30-ID" (isododecane solution of tri(trimethylsiloxy)silylpropylcarbamic acid-pullulan) and "TSPL-30-D5" (cyclopentasiloxane solution of tri(trimethylsiloxy)silylpropylcarbamic acid-pullulan) manufactured by Shin-Etsu Chemical Co., Ltd.

Examples of the silicone structure-containing silicic acid compound include a silicate compound having a silicone structure at a terminal, such as trialkyl siloxysilicate, fluorine-modified alkyl siloxysilicate, and phenyl-modified alkyl siloxysilicate.

The alkyl group in the trialkyl siloxysilicate is preferably an alkyl group having from 1 to 10 carbon atoms, more preferably from 1 to 4 carbon atoms, and is further preferably a methyl group, from the viewpoint of forming a film excellent in scratch resistance and the viewpoint of versatility. Specific examples of the trialkyl siloxysilicate include a trimethyl siloxysilicate.

Examples of the fluorine-modified alkyl siloxysilicate include a compound in which at least a part of hydrogen atoms of the alkyl groups in trialkyl siloxysilicate is substituted with a fluorine atom. Specific examples thereof include trifluoropropyldimethyl siloxysilicate and trifluoropropyldimethyl/trimethyl siloxysilicate.

Examples of the phenyl-modified alkyl siloxysilicate include phenylpropyldimethyl siloxysilicate and phenylpropyldimethyl/trimethyl siloxysilicate.

Among the silicone structure-containing silicic acid compounds, preferred are one or more selected from the group consisting of trialkyl siloxysilicate and fluorine-modified alkyl siloxysilicate from the viewpoint of forming a film excellent in scratch resistance.

As commercially available silicone structure-containing silicic acid compound, for example, trimethyl siloxysilicate (solution) such as "KF-7312J", "KF-7312K", "KF-7312T", "KF-7312L", "X-21-5249", "X-21-5250", "KF-9021", "X-21-5595", "X-21-5616", "KF-9021L", "X-21-5249L", and "X-21-5250L" each manufactured by Shin-Etsu Chemical Co., Ltd. and "XS66-B8226" (cyclopentasiloxane solution of trifluoropropyldimethyl/trimethyl siloxysilicate), "XS66-B8636" (dimethicone solution of trifluoropropyldimethyl/trimethyl siloxysilicate), and "SilShine 151" (phenylpropyldimethyl siloxysilicate) each manufactured by Momentive Performance Materials Japan LLC can be used.

Examples of the silicone dendrimer include vinyl polymers having a siloxane dendrimer structure in its side chain. Specifically, from the viewpoint of forming a film excellent in scratch resistance and the viewpoint of versatility, the siloxane dendrimer structure is preferably a group represented by the following formula (4):

(4)

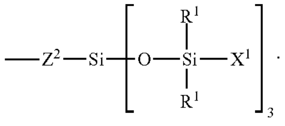

In the formula, $R^1$ is the same as above; $Z^2$ is a single bond or a divalent organic group; and $X^1$ is a group represented by the following formula (5) in which when i=1, and i is an integer of 1 or more and 10 or less indicating the hierarchy of the group.

(5)

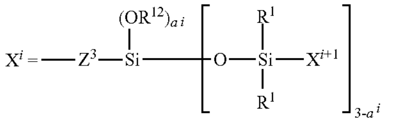

In the formula, $R^1$ is the same as above; $R^{12}$ is an alkyl group having from 1 to 10 carbon atoms; $Z^3$ is an alkylene group having from 2 to 10 carbon atoms; $X^{i+1}$ is a hydrogen atom, an alkyl group having from 1 to 10 carbon atoms, an aryl group, or a group represented by a formula (5); and i is an integer of 0 or more and 3 or less.

In the formula (4), $Z^2$ is a single bond or a divalent organic group and is preferably a divalent organic group from the viewpoint of versatility and is more preferably a divalent group represented by the following formula (6), (7), or (8):

(6)

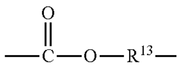

(7)

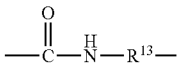

(8)

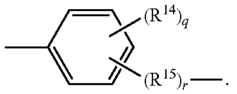

In the formulae, $R^{13}$ is an alkylene group having from 1 to 10 carbon atoms, such as a methylene group, an ethylene group, a trimethylene group, a propylene group, and a butylene group and is preferably an ethylene group, a trimethylene group, or a propylene group from the viewpoint of versatility; $R^{14}$ is an alkyl group having from 1 to 10 carbon atoms, such as a methyl group, an ethyl group, a propyl group, and a butyl group and is preferably a methyl group from the same viewpoint; $R^{15}$ is an alkylene group having from 1 to 10 carbon atoms, such as a methylene group, an ethylene group, a trimethylene group, a propylene group, and a butylene group and is preferably an ethylene group from the same viewpoint; q is an integer of 0 or more and 4 or less; and r is 0 or 1.

Examples of the vinyl polymer having the siloxane dendrimer structure in the side chain (hereinafter, also simply referred to as "vinyl polymer") include a polymer including a repeating unit derived from a monomer represented by the following formula (9):

(9)

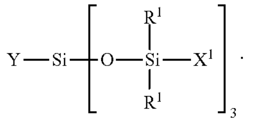

In the formula, $R^1$s and $X^1$ are the same as above; Y is a group having a vinyl bond, such as a vinyl group, a 2-acryloyloxyethyl group, a 3-acryloyloxypropyl group, a 2-methacryloyloxyethyl group, a 3-methacryloyloxypropyl group, a 4-vinylphenyl group, a 3-vinylphenyl group, a 4-(2-propenyl)phenyl group, a 3-(2-propenyl)phenyl group, a 2-(4-vinylphenyl)ethyl group, a 2-(3-vinylphenyl)ethyl group, an allyl group, and a 5-hexenyl group. Among them, from the viewpoint of versatility, preferred are a (meth)acryloyl group and a vinyl group, and more preferred is a (meth) acryloyl group.

The vinyl polymer may further include a repeating unit derived from a vinyl-based monomer other than the monomers represented by the formula (9). The vinyl-based monomer includes a group having a vinyl bond and is a monomer other than the monomers represented by the formula (9), such as (meth)acrylic acid, alkyl (meth) acrylate, hydroxyalkyl (meth) acrylate, (meth)acrylate containing an aromatic ring, fatty acid vinyl ester, (meth)acrylamide, styrene, and derivatives thereof, and one or two or more thereof can be used. Among them, from the viewpoint of versatility, preferred are (meth)acrylate-based monomers, such as (meth) acrylic acid, alkyl (meth)acrylate, hydroxyalkyl (meth)acrylate, and (meth)acrylate containing an aromatic ring.

In the vinyl polymer, the content of the repeating unit derived from the monomer represented by the formula (19) is preferably 0.1 mass % or more relative to the total repeating units in the vinyl polymer, more preferably 10 mass % or more, and further preferably 20 mass % or more, from the viewpoint of forming a film excellent in scratch resistance. The upper limit is 100 mass %.

The vinyl polymer is more preferably an acrylic polymer. That is, preferred silicone dendrimer is an acrylic polymer having a siloxane dendrimer structure in the side chain (hereinafter, also referred to as "acrylic silicone dendrimer"). The acrylic silicone dendrimer is a polymer including a repeating unit derived from a monomer in which Y is a (meth)acryloyl group in the formula (9) and may further include a repeating unit derived from a (meth)acrylic monomer other than the monomers represented by the formula (9).

Examples of commercially available silicone dendrimer include acrylic silicone dendrimer such as "FA 4001 CM Silicone Acrylate" (cyclopentasiloxane solution of acrylates/polytrimethylsiloxymethacrylate copolymer) and "FA 4002 ID Silicone Acrylate" (isododecane solution of acrylates/polytrimethylsiloxymethacrylate copolymer) each manufactured by Dow Toray Co., Ltd.

Among the above-mentioned polymers, the component (A) is more preferably one or more selected from the group consisting of silicone-modified pullulan, trimethyl siloxysilicate, trifluoropropyldimethyl/trimethyl siloxysilicate, and acrylic silicone dendrimer from the viewpoint of forming a film excellent in scratch resistance and is further preferably one or more selected from the group consisting of trimethyl siloxysilicate and acrylic silicone dendrimer.

As the component (A), silicone-based film-forming agents can be used singly or in combination of two or more thereof, and the content of the component (A) in the whole film-forming composition is, from the viewpoint of forming a film excellent in scratch resistance, 0.01 mass % or more, more preferably 0.1 mass % or more, further preferably 0.5 mass % or more, and even more preferably 1 mass % or more and preferably 10 mass % or less, more preferably 9 mass % or less, and further preferably 8 mass % or less. The content of the solid of the component (A) in the whole composition is preferably 0.01 mass % or more and 10 mass % or less, preferably 0.1 mass % or more and 9 mass % or less, more preferably 0.5 mass % or more and 8 mass % or less, and further preferably 1 mass % or more and 8 mass % or less.

The component (B) is a fiber having an average fiber diameter of 0.1 μm or more and 7 μm or less. The component (B) can form a network in the formed film, provide durability to the film, and also provide excellent scratch resistance to the formed film by being combined with the component (A) to improve the covering power and achieve a bright color.

The component (B) is present as a solid in the film-forming composition for skin, and the component (A) is present dispersed or dissolved in the film-forming composition.

Incidentally, whether a fiber forms a network in the film or not can be verified by using a scanning electron microscope (SEM). The network is a state that fibers dispersed in the film have intersections with each other to have gaps between the fibers and is a state that the component contained in the film-forming composition is retained in the gaps. The intersection of fibers is preferably a state that, for example, one fiber has two or more intersections with other two or more fibers, and the fibers are involved with each other.

The average fiber diameter is generally the diameter of a cross-section of a fiber. Here, when the cross-section of a fiber is a circle, the fiber diameter is the diameter of the circle, and when the cross-section is an ellipse, the fiber diameter is the longitudinal diameter of the ellipse. The average fiber diameter of the fiber used in the present invention is 0.1 μm or more and 7 μm or less from the viewpoint of improving the followability of the fiber to the skin in the formed film and improving the durability and the viewpoint of forming a film excellent in scratch resistance.

The average fiber diameter is preferably 0.2 μm or more and more preferably 0.3 μm or more from the viewpoint of improving the durability and the viewpoint of forming a film excellent in scratch resistance.

From the viewpoint of improving the durability and the viewpoint of forming a film excellent in scratch resistance, the average fiber diameter is preferably 6 μm or less, more preferably 5 μm or less, and further preferably 4 μm or less.

The average fiber diameter can be measured by observing fibers with an SEM at a magnification of 2000 times or 5000 times, arbitrarily selecting, from the two-dimensional image, 100 fibers excluding defects (e.g., clumps of fibers and crossing parts of fibers), drawing a line perpendicular to the longitudinal direction of each of the fibers, and directly reading the fiber diameters. The arithmetic average of these measured values is determined as the average fiber diameter. Since the fibers are dispersed in the film-forming composition, the film-forming composition is thinly applied to a substrate, and measurement by SEM observation is performed.

The length of the fiber is preferably 20 μm or more and 300 μm or less as the average fiber length from the viewpoint of a length of facilitating network formation and improving the durability of the formed film by the network and the viewpoint of forming a film excellent in scratch resistance.

The average fiber length is more preferably 25 μm or more, further preferably 30 μm or more, and further preferably 40 μm or more from the viewpoint of facilitating network formation and the viewpoint of forming a film excellent in scratch resistance.

The average fiber length is more preferably 250 μm or less and further preferably 200 μm or less from the viewpoint of suppressing tangles and twists between fibers at the time of application of the composition and the viewpoint of forming a film excellent in scratch resistance.

The average fiber length can be measured by observing fibers with an SEM at a magnification of 250 times to 750 times according to the length of the fibers, arbitrarily selecting, from the two-dimensional image, 100 fibers excluding defects (e.g., clumps of fibers and crossing parts of fibers), drawing a line in the longitudinal direction of each of the fibers, and directly reading the fiber lengths. The arithmetic average of these measured values is determined as the average fiber length.

The aspect ratio of the fiber (average fiber length)/(average fiber diameter) is preferably 10 or more and 300 or less from the viewpoint of the durability of the film by forming a uniform network and the viewpoint of forming a film excellent in scratch resistance.

The aspect ratio is more preferably 20 or more, further preferably 25 or more, and further preferably 27 or more from the viewpoint of the durability of the film and the viewpoint of forming a film excellent in scratch resistance.

The aspect ratio is more preferably 250 or less and further preferably 200 or less from the viewpoint of the durability of the film and the viewpoint of forming a film excellent in scratch resistance.

The CV (coefficient of variation) value of the fiber length of the component (B) is preferably 40% or more and 100% or less from the viewpoint that the fiber forms a network in the film.

The CV value is more preferably 42% or more and further preferably 45% or more from the viewpoint of facilitating network formation and the viewpoint of forming a film excellent in scratch resistance.

The CV value is preferably 95% or less and further preferably 90% or less from the viewpoint of enhancing the storage stability of the composition.

The CV value is calculated from the measured values obtained by the above-described fiber length-measuring method by the expression: (standard deviation of measured fiber lengths)/(average fiber length)×100(%).

The fiber of the component (B) preferably includes a fiber having a fiber length of 40 μm or more and more preferably a fiber having a fiber length of 50 μm or more from the viewpoint of forming a strong network in the film and enhancing the durability of the obtained film and the viewpoint of forming a film excellent in scratch resistance.

In the fiber of the component (B), the rate of the number of fibers having a fiber length of 40 μm or more to the total fibers is preferably 5% or more and 100% or less from the viewpoint of forming a film excellent in scratch resistance and forming a strong network in the film. The fibers having a length of 40 μm or more is more preferably contained at a rate of 8% or more and 100% or less and is further preferably contained at a rate of 15% or more and 100% or less from the viewpoint of further improving the durability and the viewpoint of forming a film excellent in scratch resistance.

This rate of the number of fibers is measured by adjusting the magnification of the SEM within ×200 to ×750 according to the fiber length such that 20 to 30 fibers are present in one imaging screen of the SEM and, in this state, measuring the fiber lengths of all fibers in the image for eliminating arbitrariness. The measurement is performed for 200 or more fibers in total.

The fiber of the component (B), i.e., the fiber of a water-insoluble polymer, can be manufactured by obtaining a fiber from a fiber-forming polymer by various known spinning technologies and subjecting the fiber for shortening treatment. Here, the fiber-forming polymer is usually a thermoplastic or solvent-soluble chain polymer molecule and is preferably a thermoplastic resin and more preferably a thermoplastic resin having a weight-average molecular weight of $1.0\times10^4$ g/mol or more and $2.0\times10^5$ g/mol or less.

As the fiber-forming polymer, a water-insoluble polymer is preferably used for maintaining the form of the fiber in a film-forming agent. The spinning method is preferably an electrospinning method for efficiently obtaining a fiber having a small fiber diameter. Specifically, solution spinning and melt spinning are mentioned.

The term "fiber of a water-insoluble polymer" refers to a fiber having a property that when 1 g of the fiber is weighed in an environment of 23° C. and 1 atm and is then immersed in 10 g of deionized water for 24 hours, the dissolved amount of the immersed fiber does not exceed 0.5 g.

Examples of the water-insoluble polymer include a completely saponified polyvinyl alcohol that can be insolubilized after film formation; a partially saponified polyvinyl alcohol that can be crosslinked after film formation by using a crosslinking agent together; oxazoline-modified silicone, such as a poly(N-propanoylethyleneimine) graft-dimethylsiloxane/γ-aminopropylmethylsiloxane copolymer; biodegradable resins, such as polyvinylacetal diethylaminoacetate, Zein (major component of corn protein), polylactic acid (PLA), polybutylene succinate, polyglycolic acid, polycaprolactone, and polyhydroxy alkanoic acid; polyester resins, such as polyethylene terephthalate (PET) and polybutylene terephthalate; acrylic resins, such as a polyacrylonitrile resin and a polymethacrylic acid resin; and a polystyrene resin, a polyvinylbutyral resin, a polyvinylacetal resin, a polyurethane resin, a polyamide resin, a polyimide resin, a polyamideimide resin, a polypropylene resin, a polyethylene resin, and various polypeptides (e.g., collagen, gelatin, fibrin, and casein). These water-insoluble polymers can be used singly or in combination of two or more thereof.

Among these water-insoluble polymers, it is preferable to use one or two or more selected from the group consisting of a completely saponified polyvinyl alcohol that can be insolubilized after film formation, a partially saponified polyvinyl alcohol that can be crosslinked after film formation by using a crosslinking agent together, a polymethacrylic acid resin and other acrylic resins, a polyvinylacetal resin, a polyurethane resin, polylactic acid, an oxazoline-modified silicone such as a poly(N-propanoylethyleneimine) graft-dimethylsiloxane/γ-aminopropylmethylsiloxane copolymer, polyvinylacetal diethylaminoacetate, and Zein.

Among them, from the viewpoint of the ease in formation of nanofibers, more preferred are one or two or more selected from the group consisting of a polyvinylbutyral resin, an acrylic resin, a polypropylene resin, a polyester such as polylactic acid, and a polyurethane resin.

The acrylic resin is preferably an (octyl acrylamide/hydroxypropyl acrylate/butylaminoethyl methacrylate) copolymer.

In addition, it is also preferable from the viewpoint of the reduction in environmental load to use a biodegradable resin such as polylactic acid, polybutylene succinate, polyglycolic acid, polycaprolactone, and polyhydroxy alkanoic acid. In the present specification, the term "biodegradability" means that the degree of biodegradation of a polyester measured in accordance with JIS K6953-1 is 30% or more.

Examples of the means for fiber shortening treatment include cutting, shearing, crushing, pulverizing, disintegrating, and defibrating. For example, it is possible to use an impact crusher such as a mechanical vortex crusher or a hammer crusher, a jet grinder such as a jet mill, a medium grinder such as a ball mill or a rod mill, a dry grinder such as a cutter mill grinder or a disc mill grinder, a media grinder using a liquid medium, a wet grinder using a medialess grinder, or a combination thereof.

In more preferred means for shortening fibers, a fiber assembly in which nanofibers are entangled, e.g., nonwoven fabric, is manufactured, the fiber assembly is then cut into an appropriate size, and then a mechanical vortex grinder, a cutter mill grinder, a disc mill grinder, a wet high-speed shear medialess grinder, or a wet high-pressure shear medialess grinder is used. Examples of the fiber assembly include, in addition to nonwoven fabric, those having a prescribed thickness, such as flocculate.

The content of the component (B) in the composition of the present invention is 0.05 mass % or more and 2 mass % or less relative to the whole film-forming composition from the viewpoint of the durability of the formed film and the ease in formation of a fiber network and the viewpoint of forming a film excellent in scratch resistance.

The content is preferably 0.1 mass % or more and more preferably 0.2 mass % or more from the viewpoint of the durability of the film and the ease in formation of a fiber network and the viewpoint of forming a film excellent in scratch resistance.

In addition, from the viewpoint of forming a stable composition, the content is preferably 1.8 mass % or less and further preferably 1.6 mass % or less.

The content of the component (B) relative to the whole film-forming composition can be determined as follows. Firstly, a fiber of a water-insoluble polymer recognized by the above-described definition of a water-insoluble polymer is obtained from the fibers contained in the composition. Secondly, the fiber is washed with a solvent in which the fiber is insoluble, and only the fiber of a water-insoluble polymer is obtained through filtration. When the resin contained in the component (B) is an ester resin such as PLA, the solvent is preferably ethanol. When the resin is acrylic, the solvent is preferably water. The obtained fiber of a water-insoluble polymer can be measured to determine the mass. The rate relative to the mass of the composition before the washing, i.e., the whole film-forming composition, can be determined by (component (B) mass after washing)/(mass of composition before washing)×100(%).

The mass ratio of the component (B) to the component (A), (B/A), in the composition of the present invention is 0.5 or more and 1 or less from the viewpoint of the durability of the film and the ease in formation of a fiber network and the viewpoint of forming a film excellent in scratch resistance.

The mass ratio (B/A) is preferably 0.06 or more, more preferably 0.08 or more, and further preferably 0.1 or more from the viewpoint of the durability of the film and forming a film excellent in scratch resistance.

The mass ratio (B/A) is preferably 0.9 or less from the viewpoint of the durability of the film and the ease in formation of a fiber network and the viewpoint of forming a film excellent in scratch resistance and more preferably 0.8 or less and further preferably 0.7 or less from the viewpoint of forming a film excellent in scratch resistance.

In the composition of the present invention, in order to form a network in the formed film and improve the durability of the film, it is preferable that the (average fiber diameter)$^2$/fiber content ($\mu m^2$/mass %) is within a range of 0.005 or more and 40 or less. The fiber content means the mass % of the fiber in the film-forming composition.

This value is preferably 0.02 or more, more preferably 0.03 or more, and further preferably 0.05 or more from the viewpoint of sufficiently forming a uniform network of the fiber.

Considering the practical blending amount, the value is preferably 35 or less, more preferably 30 or less, and further preferably 25 or less.

This value, i.e., (average fiber diameter)$^2$/fiber content ($\mu m^2$/mass %), is an index of the cumulative length of the fiber included in the composition and means that the larger this value, the shorter the cumulative length.

The composition of the present invention preferably contains a liquid substance (component (C)) selected from the group consisting of water and nonvolatile oils that are liquid at 20° C. as a dispersion medium of the component (B) in order to facilitate the formation of a network of the fiber of the component (B) in the film formed on skin when the composition of the present invention is applied to the skin.

Thus, in the film-forming composition of the present invention, since the component (B) is present dispersed or dissolved in the component (C), it becomes easy to form a network of the fiber of the component (B).

The component (C) is a liquid material selected from the group consisting of water and nonvolatile oils that are liquid at 20° C. Examples of the component (C) include water and one or two or more oils selected from the group consisting of ester oils, ether oils, hydrocarbon oils, higher alcohols, fluorine oils, and nonvolatile silicone oils. In the present invention, they are preferably used singly or in combination of two or more thereof. The volatile oil in the present invention is an oil having a vapor pressure at 20° C. of 0.01 kPa or more and 106.66 kPa or less, and the nonvolatile oil is an oil that is liquid at 20° C. other than the volatile oils.

As the ester oil, it is possible to use one or two or more selected from the group consisting of esters consisting of linear or branched fatty acid and linear or branched alcohol or polyhydric alcohol and triglycerol fatty acid esters (triglycerides).

Specifically, it is possible to used one or two or more selected from the group consisting of isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, isononyl isononanoate, isotridecyl isononanoate, cholesteryl 12-hydroxystearate, ethylene glycol di-2-ethylhexanoate, dipentaerythritol fatty acid ester, n-alkyl glycol monoisostearate, neopentyl glycol dicaprate, diisostearyl malate, glyceryl di-2-heptylundecanoate, trimethylolpropane tri-2-ethylhexanoate, trimethylolpropane triisostearate, pentaerythrityl tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalenedicarboxylate, C12-15 alkyl benzoate, cetearyl isononanoate, glyceryl tri (caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, tricoconut oil fatty acid glyceryl ester, castor oil fatty acid methyl ester, oleyl oleate, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, ethylhexyl para-methoxycinnamate, and tripropylene glycol dipivalate.

Among them, from the viewpoint of the durability of the formed film, the viewpoint of the ease in formation of a fiber network, and the viewpoint of forming a film excellent in scratch resistance, preferred are at least one selected from the group consisting of octyldodecyl myristate, myristyl myristate, isocetyl stearate, isocetyl isostearate, cetearyl isononanoate, diisobutyl adipate, di-2-ethylhexyl sebacate, isopropyl myristate, isopropyl palmitate, diisostearyl malate, neopentyl glycol dicaprate, isononyl isononanoate, isotridecyl isononanoate, glyceryl tri(caprylate/caprate), isopropyl myristate, and ethylhexyl para-methoxycinnamate, and it is more preferable to include one or two or more selected from the group consisting of diisostearyl malate, neopentyl glycol dicaprate, isononyl isononanoate, isotridecyl isononanoate, glyceryl tri(caprylate/caprate), isopropyl myristate, and ethylhexyl para-methoxycinnamate.

Examples of the ether oil include alkyl-1,3-dimethylbutyl ether such as cetyl dimethylbutyl ether, ethylene glycol dioctyl ether, glycerol monooleyl ether, and dicaprylyl ether, and one or two or more selected therefrom can be used.

As the ether oil, it is further preferable to use cetyl-1,3-dimethylbutyl ether.

Examples of the hydrocarbon oil include hydrocarbon oils that are liquid at 20° C., such as liquid paraffin, squalane, squalene, polyisobutene (pentamer or higher), and liquid isoparaffin.

Examples of the higher alcohol include higher alcohols having from 12 to 20 carbon atoms, specifically, lauryl alcohol, isostearyl alcohol, oleyl alcohol, and octyldodecanol, and one or two or more selected therefrom can be used.

Furthermore, animal and vegetable oils including the above-mentioned ester oils and hydrocarbon oils can be used. Examples of the animal and vegetable oil include olive oil, jojoba oil, macadamia nut oil, meadowfoam oil, castor oil, safflower oil, sunflower oil, avocado oil, canola oil, apricot kernel oil, rice germ oil, and rice bran oil.

Examples of the silicone oil include dimethylpolysiloxane (5 cs or more), polyether-modified silicone, amino-modified silicone, carboxy-modified silicone, methylphenylpolysiloxane, fatty acid-modified silicone, alcohol-modified silicone, aliphatic alcohol-modified silicone, epoxy-modified silicone, fluorine-modified silicone, cyclic silicone, and alkyl-modified silicone. As the silicone oil, it is preferable to use at least dimethylpolysiloxane (5 cs or more).

Examples of the fluorine oil include perfluorodecaline, perfluoroadamantane, perfluorobutyl tetrahydrofuran, perfluorooctane, perfluorononane, perfluoropentane, perfluorodecane, perfluorododecane, and perfluoropolyether.

The content of the component (C) in the composition of the present invention is preferably 5 mass % or more, more preferably 10 mass % or more, further preferably 15 mass % or more, and even more preferably 20 mass % or more considering the practical blending amount from the viewpoint of the dispersibility of the component (B) and the durability of the formed film.

In addition, considering the practical blending amount, the content is preferably 98 mass % or less, more preferably 90 mass % or less, further preferably 70 mass % or less, and even more preferably 50 mass % or less.

The content and skeletal structure of the component (C) can be identified by specifying the molecular structure by a known technology, such as NMR (nuclear magnetic resonance apparatus), chromatography, or IR analysis, or a combination thereof. The content of the component (C) can be measured by the measurement method above, for example, based on the intensity of the measured value of the portion showing the skeletal structure.

The content of water (C1) of the component (C) in the film-forming composition is preferably 1 mass % or more, more preferably 5 mass % or more, further preferably mass % or more, and even more preferably 15 mass % or more and is preferably 98 mass % or less, more preferably mass % or less, further preferably 70 mass % or less, and even more preferably 50 mass % or less from the viewpoint of the durability of the film, the viewpoint of the ease in formation of a fiber network, and the viewpoint of forming a film excellent in scratch resistance.

The mass ratio of the component (C1) to the component (C), (C1)/(C), is preferably 0.5 or more, more preferably 0.6 or more, further preferably 0.7 or more, and even more preferably 0.8 or more and is preferably or less, more preferably 0.94 or less, further preferably 0.92 or lee, and even more preferably 0.90 or less from the viewpoint of film formation and the durability of the film, the viewpoint of the ease in formation of a fiber network, and the viewpoint of forming a film excellent in scratch resistance.

The film-forming composition for skin of the present invention preferably contains a powder (component (D)) as a solid other than the component (B) in addition to the components above from the viewpoint of the excellent makeup effect of the film formed on skin, i.e., of improving the covering power of the cosmetic film and achieving a bright color excellent in color development.

The powder of the component (D) is a component providing various cosmetic effects to the film formed by using the film-forming composition of the present invention on the skin. Such a powder (D) significantly improves the covering power and can achieve a bright color excellent in color development when used together with the components (A) and (B) compared when it is used as an ordinary powder-containing cosmetic or when it is used together with a conventional fiber having a large fiber diameter.

The powder of the component (D) is not particularly limited as long as it is a powder for cosmetics, and a color pigment or an extender pigment can be used. Among them, from the viewpoint of obtaining an excellent makeup effect, it is preferable to contain a color pigment. Here, examples of the color pigment (D1) include an inorganic color pigment, an inorganic white pigment, an organic color pigment, and an organic dye and also include a pearl pigment (brilliant powder).

Examples of the inorganic color pigment contained in the composition of the present invention specifically include inorganic color pigments, such as red iron oxide, iron hydroxide, iron titanate, yellow iron oxide, black iron oxide, carbon black, Prussian blue, ultramarine blue, Prussian blue titanium oxide, black titanium oxide, a titanium/titanium oxide sintered product, manganese violet, cobalt violet, chromium oxide, chromium hydroxide, cobalt oxide, and cobalt titanate; and inorganic white pigments, such as titanium oxide, zinc oxide, calamine, zirconium oxide, magnesium oxide, cerium oxide, aluminum oxide, and composites thereof. One or two or more of them can be used.

Among them, preferred are at least one or two or more selected from the group consisting of iron oxide, titanium oxide, and zinc oxide, and more preferred one or two or more selected from the group consisting of titanium oxide, zinc oxide, red iron oxide, yellow iron oxide, and black iron oxide.

Examples of the organic color pigment and organic dye include organic tar pigments, such as Red No. 3, Red No. 102, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 405, Red No. 505, Orange No. 203, Orange No. 204, Orange No. 205, Yellow No. 4, Yellow No. 5, Yellow No. 401, Blue No. 1, and Blue No. 404; and organic dyes, such as β-carotene, caramel, and a paprika dye. In addition, the examples include those coated with polymers such as cellulose or polymethacrylate ester.

Examples of the pearl pigment (brilliant powder) include fish scale foil, titanium oxide-coated mica (mica titanium), bismuth oxychloride, titanium oxide-coated bismuth oxychloride, titanium oxide-coated talc, titanium oxide-coated colored mica, titanium oxide/iron oxide-coated mica, fine particle titanium oxide-coated mica titanium, fine particle zinc oxide-coated mica titanium, organic pigment-treated mica titanium, low-order titanium oxide-coated mica, titanium oxide-coated synthetic mica, titanium oxide-coated plate-like silica, hollow plate-like titanium oxide, iron oxide-coated mica, plate-like iron oxide (MIO), aluminum flake, stainless steel flake, titanium oxide-coated plate-like alumina, glass flake, titanium oxide-coated glass flake, pearl shell, gold foil, a gold-deposited resin film, and a metal-deposited resin film. One or two or more of them can be used.

Examples of the extender pigment include inorganic extender pigments and organic extender pigments.

Examples of the inorganic extender pigment include barium sulfate, calcium sulfate, magnesium sulfate, magnesium carbonate, calcium carbonate, talc, mica, kaolin, sericite, silicic acid, silicic anhydride, aluminum silicate, magnesium silicate, magnesium aluminum silicate, calcium silicate, barium silicate, strontium silicate, metal tungstate, hydroxyapatite, vermiculite, clay, bentonite, montmorillonite, hectorite, smectite, zeolite, ceramic powder, dicalcium phosphate, alumina, silica, aluminum hydroxide, boron nitride, synthetic mica, synthetic sericite, metallic soap, and barium sulfate-treated mica. One or two or more of them can be used.

Examples of the organic extender pigment include a silicone rubber powder, a silicone resin-coated silicone rubber powder, polymethylsilsesquioxane, a polyamide powder, a nylon powder, a polyester powder, a polypropylene powder, a polystyrene powder, a polyurethane powder, a vinyl resin powder, a urea resin powder, a phenolic resin powder, a fluorine resin powder, a silicone resin powder, an acrylic resin powder, a melamine resin powder, a polycarbonate resin, a divinylbenzene/styrene copolymer, a silk powder, a wool powder, a cellulose powder, a long-chain alkyl phosphate metal salt, N-mono (long-chain) alkylacyl basic amino acid, and composites thereof. One or two or more of them can be used.

In addition, the examples include composite powders of the inorganic powder and the organic powder.

The particle diameter of the powder is preferably 0.01 μm or more and 500 μm or less, more preferably 0.02 μm or more and 100 μm or less, further preferably 0.03 μm or more and 10 μm or less, and even more preferably 0.03 μm or more and 2 μm or less.

Examples of the shape of the powder include spherical, plate-like, granular, and amorphous. In the plate-like shape here, the aspect ratio (average length/average thickness) is preferably less than 20, more preferably less than 15, and further preferably less than 10.

The powders can also be used after hydrophobic treatment, and one or two or more of these powders hydrophobized can also be used. The hydrophobic treatment is not limited as long as it is treatment that is applied to ordinary powders for cosmetics, and may be performed by using a surface treatment agent such as a silicone compound, an alkylsilane, metal soap, an amino acid compound, lecithin, organic titanate, a fluorine compound, an acrylic resin, a methacrylic resin, or a urethane resin by dry treatment, wet treatment, or the like.

As the hydrophobic treatment, preferred are surface treatment, examples include treatment with a silicone compound such as dimethylpolysiloxane, methyl hydrogen polysiloxane, cyclic silicone, or one-terminal or both-terminal trialkoxy group-modified organopolysiloxane; treatment with an alkylsilane such as methyltrimethoxysilane, ethyltrimethoxysilane, hexyltrimethoxysilane, caprylyl trimethoxysilane, or caprylyl triethoxysilane; treatment with metal soap such as aluminum stearate, aluminum myristate, zinc stearate, or magnesium stearate; treatment with an amino acid compound such as proline, hydroxyproline, alanine, glycine, sarcosine, glutamic acid, aspartic acid, lysine, or a derivative thereof; lecithin treatment; treatment with an organic titanate such as isopropyl titanium triisostearate; treatment with a fluorine compound such as perfluoroalkyl alkoxysilane, fluorine-modified silicone, perfluoropolyether, or perfluoroalkyl phosphate; and acrylic resin treatment, methacrylic resin treatment, and urethane resin treatment. In particular, powders surface-treated with a silicone compound, an alkylsilane, or an amino acid compound are more preferable.

The content of the component (D) powder in the film-forming composition for skin of the present invention is preferably 0.5 mass % or more, more preferably 1 mass % or more, and further preferably 5 mass % or more from the viewpoint of improving the durability of the film and the viewpoint of improving the covering power and achieving a bright color excellent in color development. In addition, from the same viewpoint, the content is preferably 94 mass % or less, more preferably 60 mass % or less, further preferably 50 mass % or less, and even more preferably 40 mass % or less.

The component (D) powder preferably contains a color pigment (D1) as described above, and the content of the color pigment in the film-forming composition for skin of the present invention is preferably 0.1 mass % or more and 60 mass % or less from the viewpoint of obtaining an excellent makeup effect. The content is more preferably 0.3 mass % or more, further preferably 1 mass % or more and is more preferably 50 mass % or less, further preferably 40 mass % or less, and preferably 30 mass % or less.

The content mass ratio of the color pigment (D1) to the component (D), (D1/D), is preferably 0.3 or more, more preferably 0.4 or more, and further preferably 0.5 or more. In addition from the same viewpoint, the mass ratio is preferably 1 or less, more preferably 0.9 or less, and further preferably 0.8 or less.

The composition of the present invention can further contain an oil other than the component (C), a volatile component, a surfactant, a polyol that is liquid at 20° C., a preservative, a moisturizing agent, an ultraviolet absorber, a water-soluble polymer, an amino acid, a dye, and so on.

The oil other than the component (C) is not limited as long as it is solid or semisolid at 20° C. and is used in ordinary cosmetics, and examples thereof include mineral-based waxes such as ozokerite and ceresin; petroleum waxes such as paraffin and microcrystalline wax; synthetic hydrocarbons such as Fischer-Tropsch wax, polyethylene wax, and synthetic hydrocarbon wax; vegetable waxes such as carnauba wax, candelilla wax, rice wax, sunflower wax, and highly hydrogenated jojoba oil; animal waxes such as beeswax Chinese wax, and whale wax; and synthetic waxes such as silicone wax and synthetic beeswax.

Examples of the volatile component include alcohols, ketones, volatile silicone oils, and volatile hydrocarbon oils, and preferred are one or more selected from the group consisting of alcohols, volatile silicone, and volatile hydrocarbon oils. The volatile component is a material having volatility in the liquid state. The volatile material has a vapor pressure at 20° C. of 0.01 kPa or more and 106.66 kPa or less.

As the volatile alcohol, for example, a monovalent chain aliphatic alcohol, a monovalent cyclic aliphatic alcohol, or a monovalent aromatic alcohol is suitably used. Examples of the monovalent chain aliphatic alcohol include $C_1$-$C_6$ chain alcohols, examples of the monovalent cyclic aliphatic alcohol include $C_4$-$C_6$ cyclic alcohols, and examples of the monovalent aromatic alcohol include benzyl alcohol and phenylethyl alcohol. Specific examples thereof include ethanol, isopropyl alcohol, butyl alcohol, phenylethyl alcohol, n-propanol, and n-pentanol. From the viewpoint of use impression, ethanol is preferable. These alcohols can be used alone or in combination of two or more.

Examples of the volatile silicone oil include linear dimethylpolysiloxanes, such as hexamethyldisiloxane (dimethylpolysiloxane (0.65 cs)), octamethyltrisiloxane (dimethylpolysiloxane (1 cs)), dimethylpolysiloxane (1.5 cs), and dimethylpolysiloxane (2 cs); branched siloxanes, such as methyl trimethicone, tris(trimethylsilyl)methylsilane, and tetrakis(trimethylsilyl)silane; and cyclic dimethylsiloxanes, such as octamethylcyclotetrasiloxane, decamethylcyclopentasiloxane, and dodecamethylcyclohexasiloxane.

Among them, from the viewpoint of excellent use impression and finish, preferred are linear dimethylpolysiloxanes and branched siloxane, and it is more preferable to include one or two or more selected from the group consisting of hexamethyldisiloxane (dimethylpolysiloxane (0.65 cs)), octamethyltrisiloxane (dimethylpolysiloxane (1 cs)), dimethylpolysiloxane (1.5 cs), dimethylpolysiloxane (2 cs), and methyl trimethicone, further preferable to at least include one or two or more selected from the group consisting of hexamethyldisiloxane (dimethylpolysiloxane (0.65 cs)), octamethyltrisiloxane (dimethylpolysiloxane (1 cs)), and methyl trimethicone, and even more preferable to at least include one or two or more selected from the group consisting of hexamethyldisiloxane (dimethylpolysiloxane (0.65 cs)), and octamethyltrisiloxane (dimethylpolysiloxane (1 cs)).

Examples of the volatile hydrocarbon oil include paraffin-based hydrocarbon oils, such as n-decane, n-undecane, and n-dodecane; isoparaffin-based hydrocarbon oils, such as isodecane, isododecane, and hydrogenated polyisobutene; and cyclic paraffin hydrocarbon oils, such as cyclodecane and cyclododecane. Among them, from the viewpoint of excellent use impression and suppressing unevenness of the finish, preferred are isoparaffin-based hydrocarbon oils, more preferred are isoparaffin-based hydrocarbon oils having from 8 to 16 carbon atoms, further preferred are isoparaffin-based hydrocarbon oils having from 10 to 16 carbon atoms, and it is even more preferable to at least include isododecane.

As the volatile oil, it is preferable to include one or two or more selected from the group consisting of isododecane and dimethylpolysiloxane having a kinematic viscosity at 25° C. of 2 cSt or less from the viewpoint of excellent use impression and finish. Incidentally, the kinematic viscosity can be measured by using, for example, an Ubbelohde viscometer.

The content of the volatile component in the composition of the present invention is preferably 1 mass % or more relative to the whole film-forming composition, more preferably 10 mass % or more, further preferably 25 mass % or more and preferably 60 mass % or less, more preferably 50 mass % or less, and further preferably 45 mass % or less from the viewpoint of improving the durability of the film and the viewpoint of improving the covering power and achieving a bright color excellent in color development.

Examples of the surfactant include nonionic surfactants, anionic surfactants, and cationic surfactants, and particularly preferred are nonionic surfactants, such as a polyoxyethylene/methylpolysiloxane copolymer, a poly(oxyethylene/oxypropylene)methylpolysiloxane copolymer, crosslinked polyether-modified silicone, crosslinked alkylpolyether-modified silicone, cetyl dimethicone copolyol, sorbitan monooleate, glyceryl stearate, polyoxyethylene hydrogenated castor oil, polyoxyethylene alkyl ether, sorbitan sesquioleate, and diglyceryl monooleate. These surfactants may be used singly or in combination of two or more thereof.

The content of the surfactant in the composition of the present invention is preferably 0.01 mass % or more relative to the whole film-forming composition, more preferably 0.1 mass % or more, and further preferably 0.3 mass % or more and preferably 10 mass % or less, more preferably 5 mass % or less, and further preferably 3 mass % or less from the viewpoint of improving the durability of the film and the viewpoint of improving the covering power and achieving a bright color excellent in color development.

Examples of the polyol that is liquid at 20° C. include alkylene glycols, such as ethylene glycol, propylene glycol, 1,3-propanediol, and 1,3-butanediol; polyalkylene glycols, such as diethylene glycol, dipropylene glycol, and polyethylene glycol and polypropylene glycol each having a weight-average molecular weight of 2000 g/mol or less; and glycerins, such as glycerin, diglycerin, and triglycerin.

Among them, preferred are ethylene glycol, propylene glycol, 1,3-butanediol, dipropylene glycol, polyethylene glycol having a weight-average molecular weight of 2000 g/mol or less, glycerin, and diglycerin; more preferred are propylene glycol, 1,3-butanediol, and glycerin; and further preferred are propylene glycol and 1,3-butanediol.

Examples of the form of the film-forming composition for skin of the present invention include oily cosmetics and emulsified cosmetics, specifically, oily cosmetics, water-in-oil emulsified cosmetics, and oil-in-water emulsified cosmetics. In particular, emulsified cosmetics are preferable, and water-in-oil emulsified cosmetics are more preferable. The composition of the present invention can be manufactured by heating the components as needed and mixing them according to a usual method.

The film-forming composition for skin of the present invention can be applied as, for example, makeup cosmetics, such as a makeup base, a foundation, a concealer, a blusher, an eyeshadow, a mascara, an eyeliner, an eyebrow, an overcoat agent, and a lipstick; ultraviolet protection cosmetics, such as a sunscreen emulsion and a sunscreen cream; and skincare cosmetics, such as a lotion, an emulsion, a cream, a serum, and a facial mask and is suitable as a makeup cosmetic or an ultraviolet protection cosmetic.

The composition of the present invention is a film-forming composition for skin and can form a uniform film on a skin surface by being applied to the skin. In this film, the fiber forms a network, the network of the fiber is strengthened by the component (A) to provide excellent durability to the film, and the scratch resistance of the obtained film is significantly improved. When the film is used as a cosmetic film, the covering power by the cosmetic film is also improved, and a bright color excellent in color development can be achieved.

A cosmetic film excellent in durability can be formed on a skin surface by applying the composition of the present invention to the skin. Examples of means for applying the composition to the skin include finger application, spray application, application by using a tool such as a roller or sponge, and application in a form of a stick-shaped solid cosmetic.

The film formed on a skin surface by the present invention not only has excellent durability but also has significantly improved scratch resistance, and when used as a cosmetic film, the covering power by the cosmetic film is also improved, and a bright color excellent in color development can be achieved.

Here, the thickness of the film varies depending on the application amount and is, in a usual use (an application basis weight of 1 $mg/cm^2$ or more and 3 $mg/cm^2$ or less), preferably 0.3 μm or more and 30 μm or less and more preferably 0.5 μm or more and 20 μm or less. The thickness is measured after application to a substrate with a contact coating thickness gauge (manufactured by Mitutoyo Corporation, Litematic VL-50A) on the substrate. Incidentally, the substrate used here is made of PET.

Regarding the above-described embodiments, the present invention further discloses the following composition, producing method, and film.

<1> A film-forming composition for skin comprising the following components (A) and (B);
   (A) a silicone-based film-forming agent; and
   (B) a fiber having an average fiber diameter of 0.1 μm or more and 7 μm or less in an amount of 0.05 mass % or more and 2 mass % or less relative to the whole film-forming composition, wherein
   the mass ratio of the component (B) to the component (A), (B/A), is 0.05 or more and 1 or less.

<2> The film-forming composition for skin according to <1>, wherein the component (B) is a fiber of a water-insoluble polymer.

<3> The film-forming composition for skin according to <1> or <2>, wherein the component (B) has an aspect ratio (average fiber length/average fiber diameter) of 10 or more and 300 or less.

<4> The film-forming composition for skin according to any of <1> to <3>, wherein the content of the component (A) relative to the whole film-forming composition is 0.01 mass % or more and 10 mass % or less.

<5> The film-forming composition for skin according to any of <1> to <4>, further containing a component (C) nonvolatile liquid material.

<6> The film-forming composition for skin according to any of <1> to <5>, further containing a component (D) powder.

<7> The film-forming composition for skin according to any of <1> to <6>, wherein the component (A) is one or more selected from the group consisting of silicone-modified pullulan, silicone structure-containing silicic acid compounds, and silicone dendrimer.

<8> The film-forming composition for skin according to any of <1> to <7>, wherein the component (A) is more preferably one or more selected from the group consisting of silicone-modified pullulan, trimethyl siloxysilicate, trifluoropropyldimethyl/trimethyl siloxysilicate, and acrylic silicone dendrimer and is further preferably one or more selected from the group consisting of trimethyl siloxysilicate and acrylic silicone dendrimer.

<9> The film-forming composition for skin according to any of <1> to <8>, wherein the content of the solid in the component (A) relative to the whole film-forming composition is preferably 0.1 mass % or more and 9 mass % or less, more preferably 0.5 mass % or more and 8 mass % or less, and further preferably 1 mass % or more and 8 mass % or less.

<10> The film-forming composition for skin according to any of <1> to <9>, wherein the component (B) has an average fiber diameter of 0.2 μm or more and 5 μm or less, preferably 0.3 μm or more and 4 μm or less, and further preferably 0.3 μm or more and 3 μm or less.

<11> The film-forming composition for skin according to any of <1> to <10>, wherein the component (B) is a fiber of a water-insoluble polymer.

<12> The film-forming composition for skin according to any of <1> to <11>, wherein the component (B) is a fiber including one or two or more polymers selected from the group consisting of a completely saponified polyvinyl alcohol that can be insolubilized after film formation, a partially saponified polyvinyl alcohol that can be crosslinked after film formation by using a crosslinking agent together, acrylic resins such as polymethacrylic acid resin, a polyvinylbutyral resin, a polyurethane resin, polylactic acid, an oxazoline-modified silicone such as a poly(N-propanoylethyleneimine) graft-dimethylsiloxane/γ-aminopropylmethylsiloxane copolymer, polyvinylacetal diethylaminoacetate, and zein; and is preferably a fiber including one or two or more polymers selected from the group consisting of a polyvinylbutyral resin, an acrylic resin, a polypropylene resin, a polyurethane resin, polylactic acid, polybutylene succinate, polyglycolic acid, polycaprolactone, and polyhydroxy alkanoic acid.

<13> The film-forming composition for skin according to any of <1> to <12>, wherein the component (B) is a fiber including an (octyl acrylamide/hydroxypropyl acrylate/butylaminoethyl methacrylate) copolymer.

<14> The film-forming composition for skin according to any of <1> to <13>, wherein the component (B) has an average fiber length of 20 μm or more and 300 μm or less, preferably 25 μm or more and 250 μm or less, more preferably 30 μm or more and 200 μm or less, and further preferably 40 μm or more and 200 μm or less.

<15> The film-forming composition for skin according to any of <1> to <14>, wherein the component (B) has an aspect ratio (average fiber length/average fiber diameter) of 20 or more and 250 or less, preferably 25 or more and 200 or less, and more preferably 27 or more and 200 or less.

<16> The film-forming composition for skin according to any of <1> to <15>, wherein the CV value of the fiber length of the component (B) is 40% or more and 100% or less, preferably 42% or more and 95% or less, and more preferably 45% or more and 90% or less.

<17> The film-forming composition for skin according to any of <1> to <16>, wherein the component (B) includes a fiber having an average fiber length of 40 μm or more, preferably 50 μm or more.

<18> The film-forming composition for skin according to any of <1> to <17>, wherein the (average fiber diameter)$^2$/fiber content (μm$^2$/mass %) in the composition is 0.02 or more and 7 or less, preferably 0.02 or more and 6 or less, more preferably 0.03 or more and 5 or less, and further preferably 0.05 or more and 4 or less.

<19> The film-forming composition for skin according to any of <1> to <18>, wherein the content of the component (B) is 0.1 mass % or more and 1.8 mass % or less, preferably 0.2 mass % or more and 1.8 mass % or less, more preferably 0.2 mass % or more and 1.6 mass % or less.

<20> The film-forming composition for skin according to any of <1> to <19>, wherein the mass ratio of the component (B) to the component (A), (B/A), is 0.06 or more and 0.9 or less, preferably 0.08 or more and 0.7 or less, and more preferably 0.1 or more and 0.7 or less.

<21> The film-forming composition for skin according to any of <5> to <20>, wherein the component (C) is preferably one or more selected from the group consisting of water and oils that are liquid at 20° C.

<22> The film-forming composition for skin according to any of <5> to <20>, wherein the component (C) is water and one or two or more oils selected from the group consisting of ester oils, ether oils, hydrocarbon oils, higher alcohols, fluorine oils, and nonvolatile silicone oils.

<23> The film-forming composition for skin according to any of <5> to <22>, wherein the component (B) is preferably dispersed in the component (C).

<24> The film-forming composition for skin according to any of <6> to <23>, wherein the component (D) is one or two or more selected from the group consisting of extender pigments and color pigments and includes a color pigment.

<25> The film-forming composition for skin according to any of <6> to <24>, wherein the component (D) includes one or two or more color pigments selected from the group consisting of inorganic color pigments, inorganic white pigments, organic color pigments, organic dyes, and pearl pigments (brilliant powders).

<26> The film-forming composition for skin according to any of <6> to <25>, wherein the component (D) contains a color pigment, and the content of the color pigment in the film-forming composition is 0.1 mass % or more and 60 mass % or less.

<27> The film-forming composition for skin according to any of <6> to <26>, wherein the content mass ratio of the color pigment (D1) to the component (D), (D1/D), is 0.3 or more and 1 or less.

<28> The film-forming composition for skin according to any of <1> to <27>, wherein the component (B) is a biodegradable resin.

<29> A method for producing a film on a skin surface, comprising applying the film-forming composition according to any of <1> to <28> to the skin.

<30> A film including the film-forming composition for skin according to any of <1> to <28>.

<31> Use of the film-forming composition for skin according to any one of <1> to <28> as an emulsified cosmetic.

<32> Use of the film-forming composition according to any one of <1> to <28> for makeup and/or ultraviolet protection by applying the composition to skin, preferably, to the face.

<33> Use of the film-forming composition for skin according to any one of <1> to <28> for producing a cosmetic film on a skin surface.

EXAMPLES

The present invention will now be described in further detail with reference to examples.

Production Example of Component (B)

A production example of a fiber B will be shown.

(1) An acrylic resin ((octyl acrylamide/hydroxypropyl acrylate/butylaminoethyl methacrylate) copolymer) was dissolved in ethanol to obtain an 18 mass % solution. A nanofiber sheet was formed on the surface of a collector, by using this solution with the device for an electrospinning method shown in FIG. 1. The conditions for manufacturing the nanofiber are as follows: Applied voltage: 30 kV; Capillary-collector distance: 150 mm; Aqueous solution discharge amount: 12 mL/hour; and Environment: 25° C., 30% RH.

(2) The obtained nanofiber sheet was appropriately cut and was then pulverized with an agitation system (manufactured by PRIMIX Corporation, LABOLUTION (registered trademark)) attached with dispersal blades at a rotational speed of 5000 rpm for 30 minutes to obtain a fiber B.

Fibers A and C to F were manufactured as with the fiber B by changing the polymer concentration, rotational speed, and shearing time.

A production example of a fiber G will be shown. (1) An ester resin (polylactic acid) was dissolved in a mixture of chloroform and dimethylformamide (mass ratio=80:20) to obtain a 20 mass % solution. A nanofiber sheet was formed on the surface of a collector, by using this solution with the device for an electrospinning method shown in FIG. 1. The conditions for manufacturing the nanofiber are as follows: Applied voltage: 30 kV; Capillary-collector distance: 150 mm; Aqueous solution discharge amount: 12 mL/hour; and Environment: 25° C., 30% RH.

(2) The obtained nanofiber sheet was sheared by using a dispersion device (manufactured by Pacific Machinery & Engineering Co., Ltd, Milder) at 13500 rpm and circulating 8 times in a circulation line to obtain a fiber.

Fiber H was manufactured as in the fiber G by changing the polymer concentration and circulation number.

Production Example of Composition

Water-in-oil emulsified compositions were obtained by blending the obtained fibers and the components shown in Tables 1 to 4.

Examples 1 to 13 and Comparative Examples 1 to 5

The water-in-oil emulsified compositions of Tables 1 to 4 were applied to artificial leather, and the scratch resistance, covering effect, and color development performance of the films were evaluated. The results are shown in Tables 1 to 4.

(Evaluation Method)

[Covering Effect]

A sample was spread on black artificial leather (Saplare: manufactured by Idemitsu Technofine Co., Ltd.) with an applicator of 25 μm and was dried on a hotplate at 40° C. and was further dried at room temperature overnight.

The color was measured with a colorimeter (CR-400, manufactured by KONICA MINOLTA, INC.). The difference between the lightness (L* value) of the black artificial leather before the application and the lightness of the sample was taken as how much the black color of the artificial leather as a reference was brightened by a film was determined as the covering effect. The average value of 5 points was adopted.

[Color Development Performance]

A sample was spread on black artificial leather (Saplare: manufactured by Idemitsu Technofine Co., Ltd.) with an applicator of 25 μm and was dried on a hotplate at 40° C. and was dried at room temperature overnight. The color was measured with a colorimeter (CR-400, manufactured by KONICA MINOLTA, INC.). The saturation was adopted for grasping how bright (the degree of color development) the film was formed by using the comparative example A not blended with disintegrated fine fibers as a reference. The average value of 5 points was adopted.

$$\text{Saturation}=((a_{sample}{}^*-a_{black\ leather}{}^*)^2+(b_{sample}{}^*-b_{black\ leather}{}^*)^2)^{0.5} \quad \text{[Math 1]}$$

[Scratch Resistance]

A sample was spread on black artificial leather (Laforet: manufactured by Teijin Cordley Limited) with an applicator of 152 μm and was dried on a hotplate at 40° C. and was dried at room temperature overnight.

The sample surface was rubbed in one direction with the middle finger of the right hand. On this occasion, the middle finger of the right hand was wiped with a tissue each time. The number of rubs was counted until the film removed by the rubbing.

TABLE 1

| | | | Example 1 | Example 2 | Example 3 | Example 4 | Example 5 | Example 6 |
|---|---|---|---|---|---|---|---|---|
| | (B) Fiber | Polymer material | Fiber A Acrylic resin | Fiber B Acrylic resin | Fiber C Acrylic resin | Fiber B Acrylic resin | Fiber D Acrylic resin | Fiber B Acrylic resin |
| | | Fiber diameter (μm) | 0.3 | 0.6 | 0.6 | 0.6 | 0.6 | 0.6 |
| | | Fiber length (μm) | 50 | 50 | 20 | 50 | 100 | 50 |
| | | Aspect ratio | 166.7 | 83.3 | 33.3 | 83.3 | 166.7 | 83.3 |
| | | Rate of the number of fibers having a fiber length of 40 μm or more (%) | 52.3 | 54.3 | 10.1 | 54.3 | 78.3 | 54.3 |
| | Raw material | | Acrylic resin | Acrylic resin | Acrylic resin | Acrylic resin | Acrylic resin | Acrylic resin |
| Oil phase | (A) Silicone-based film-forming agent | Trimethyl siloxysilicate (manufactured by Shin-Etsu Chemical Co., Ltd., Silicone KF-7312J, 50% D5 solution) | 4.00 | 4.00 | 4.00 | 4.00 | 4.00 | |
| | | Acrylic silicone dendrimer (manufactured by Dow Toray Co., Ltd., DOWSIL FA 4001 | | | | | | 6.00 |

TABLE 1-continued

| | | | | | | | | | |
|---|---|---|---|---|---|---|---|---|---|
| | | | CM, 30% D5 solution) | | | | | | |
| | (B) Fiber | | Each fiber above | 1.00 | 0.50 | 1.00 | 1.00 | 1.00 | 1.00 |
| | (C) Water and | | Octyl p-methoxycinnamate | 3.00 | 3.00 | 3.00 | 3.00 | 3.00 | 3.00 |
| Water phase | nonvolatile oil that is liquid at 20° C. | | Purified water | 20.00 | 20.00 | 20.00 | 20.00 | 20.00 | 20.00 |
| Oil phase | Surfactant | | Polyether-modified silicone (DOWSIL SH3775M FLUID) | 0.40 | 0.40 | 0.40 | 0.40 | 0.40 | 0.40 |
| | | | Dimethylsiloxane/methyl (undecyl glyceryl ether) siloxane copolymer (JP-A-2015-107926, Production example 2) | 0.10 | 0.10 | 0.10 | 0.10 | 0.10 | 0.10 |
| | (E) Volatile oil | | Dimethylpolysiloxane (manufactured by Shin-Etsu Chemical Co., Ltd., Silicone KF-96L-2CS) | 41.00 | 41.50 | 41.00 | 41.00 | 41.00 | 39.00 |
| Water phase | Other component | | Ethanol | 5.00 | 5.00 | 5.00 | 5.00 | 5.00 | 5.00 |
| | | | Magnesium sulfate | 0.50 | 0.50 | 0.50 | 0.50 | 0.50 | 0.50 |
| Powder phase | (D) Powder | (D1) Color pigment | Silicone-treated titanium oxide (manufacture by ISHIHARA SANGYOU KAISHA, LTD., CR-50, average particle diameter: 0.25 μm) | 10.00 | 10.00 | 10.00 | 10.00 | 10.00 | 10.00 |
| | | | Silicone-treated yellow iron oxide | 2.00 | 2.00 | 2.00 | 2.00 | 2.00 | 2.00 |
| | | | Silicone-treated red iron oxide | 0.40 | 0.40 | 0.40 | 0.40 | 0.40 | 0.40 |
| | | | Silicone-treated black iron oxide | 0.20 | 0.20 | 0.20 | 0.20 | 0.20 | 0.20 |
| | | | Silicone-treated fine particle zinc oxide (manufactured by TAYCA Corp. MZY-505M) 25 nm | 3.00 | 3.00 | 3.00 | 3.00 | 3.00 | 3.00 |
| | | Extender pigment | Urethane powder | 3.00 | 3.00 | 3.00 | 3.00 | 3.00 | 3.00 |
| | | | Silicone-coated talc (JA-46R LHC) | 6.40 | 6.40 | 6.40 | 6.40 | 6.40 | 6.40 |
| Total amount | | | | 100.00 | 100.00 | 100.00 | 100.00 | 100.00 | 100.00 |
| (A) Silicone-based film-forming agent | | | | 2.00 | 2.00 | 2.00 | 2.00 | 2.00 | 1.80 |
| (B) Fiber | | | | 1.00 | 0.50 | 1.00 | 1.00 | 1.00 | 1.00 |
| (C) Water and nonvolatile oil that is liquid at 20° C. | | | | 23.00 | 23.00 | 23.00 | 23.00 | 23.00 | 23.00 |
| (D) Powder | | | | 25.00 | 25.00 | 25.00 | 25.00 | 25.00 | 25.00 |
| (E) Volatile oil | | | | 41.00 | 41.50 | 41.00 | 41.00 | 41.00 | 39.00 |
| Surfactant | | | | 0.50 | 0.50 | 0.50 | 0.50 | 0.50 | 0.50 |
| (B) (Average fiber diameter)$^2$/fiber content | | | | 0.09 | 0.72 | 0.36 | 0.36 | 0.36 | 0.36 |
| (B)/(A) | | | | 0.50 | 0.25 | 0.50 | 0.50 | 0.50 | 0.56 |
| Evaluation result | | Covering effect (the difference ΔL from black artificial leather painted black) | | 39.55 | 42.30 | 42.18 | 42.89 | 41.10 | 42.39 |
| | | Color development performance (bright color, increased saturation compared to Comparative Example A as reference | | 7.13 | 9.40 | 9.63 | 9.80 | 8.03 | 11.25 |
| | | Scratch resistance | | ≥30 | 25 | 21 | ≥30 | ≥30 | 17 |

| | | | | Example 7 | Example 8 | Example 9 | Comparative Example A |
|---|---|---|---|---|---|---|---|
| | (B) Fiber | | Polymer material | Fiber E Acrylic resin | Fiber F Acrylic resin | Fiber G PLA | None |
| | | | Fiber diameter (μm) | 1.8 | 5.0 | 1.5 | |
| | | | Fiber length (μm) | 50 | 50 | 50 | |
| | | | Aspect ratio | 27.8 | 10.0 | 33.3 | |
| | | | Rate of the number of fibers having a fiber length of 40 μm or more (%) | 70.9 | 80.4 | 40.0 | |
| | Raw material | | | Acrylic resin | Acrylic resin | PLA | None |
| Oil phase | (A) Silicone-based film-forming agent | | Trimethyl siloxysilicate (manufactured by Shin-Etsu Chemical Co., Ltd., Silicone KF-7312J, 50% D5 solution) | 4.00 | 4.00 | 4.00 | 4.00 |
| | | | Acrylic silicone dendrimer (manufactured by Dow Toray Co., Ltd., DOWSIL FA 4001 CM, 30% D5 solution) | | | | |
| | (B) Fiber | | Each fiber above | 1.00 | 1.00 | 1.00 | — |
| | (C) Water and | | Octyl p-methoxycinnamate | 3.00 | 3.00 | 3.00 | 3.00 |
| Water phase | nonvolatile oil that is liquid at 20° C. | | Purified water | 20.00 | 20.00 | 20.00 | 20.00 |
| Oil phase | Surfactant | | Polyether-modified silicone (DOWSIL SH3775M FLUID) | 0.40 | 0.40 | 0.40 | 0.40 |
| | | | Dimethylsiloxane/methyl (undecyl glyceryl ether) siloxane copolymer (JP-A-2015-107926, Production example 2) | 0.10 | 0.10 | 0.10 | 0.10 |
| | (E) Volatile oil | | Dimethylpolysiloxane (manufactured by Shin-Etsu Chemical Co., Ltd., Silicone KF-96L-2CS) | 41.00 | 41.00 | 41.00 | 42.00 |
| Water phase | Other component | | Ethanol | 5.00 | 5.00 | 5.00 | 5.00 |
| | | | Magnesium sulfate | 0.50 | 0.50 | 0.50 | 0.50 |
| Powder phase | (D) Powder | (D1) Color pigment | Silicone-treated titanium oxide (manufacture by ISHIHARA SANGYOU KAISHA, LTD., CR-50, average particle | 10.00 | 10.00 | 10.00 | 10.00 |

TABLE 1-continued

| | | | | | | |
|---|---|---|---|---|---|---|
| | | diameter: 0.25 μm) | | | | |
| | | Silicone-treated yellow iron oxide | 2.00 | 2.00 | 2.00 | 2.00 |
| | | Silicone-treated red iron oxide | 0.40 | 0.40 | 0.40 | 0.40 |
| | | Silicone-treated black iron oxide | 0.20 | 0.20 | 0.20 | 0.20 |
| | | Silicone-treated fine particle zinc oxide (manufactured by TAYCA Corp. MZY-505M) 25 nm | 3.00 | 3.00 | 3.00 | 3.00 |
| | Extender pigment | Urethane powder | 3.00 | 3.00 | 3.00 | 3.00 |
| | | Silicone-coated talc (JA-46R LHC) | 6.40 | 6.40 | 6.40 | 6.40 |
| Total amount | | | 100.00 | 100.00 | 100.00 | 100.00 |
| (A) Silicone-based film-forming agent | | | 2.00 | 2.00 | 2.00 | 2.00 |
| (B) Fiber | | | 1.00 | 1.00 | 1.00 | — |
| (C) Water and nonvolatile oil that is liquid at 20° C. | | | 23.00 | 23.00 | 23.00 | 23.00 |
| (D) Powder | | | 25.00 | 25.00 | 25.00 | 25.00 |
| (E) Volatile oil | | | 41.00 | 41.00 | 41.00 | 42.00 |
| Surfactant | | | 0.50 | 0.50 | 0.50 | 0.50 |
| (B) (Average fiber diameter)$^2$/fiber content | | | 3.24 | 25.00 | 2.25 | — |
| (B)/(A) | | | 0.50 | 0.50 | 0.50 | — |
| Evaluation result | Covering effect (the difference ΔL from black artificial leather painted black) | | 40.95 | 41.98 | 38.90 | 28.64 |
| | Color development performance (bright color, increased saturation compared to Comparative Example A as reference | | 8.14 | 9.19 | 6.86 | 0.00 |
| | Scratch resistance | | ≥30 | ≥30 | ≥30 | 11 |

TABLE 2

| | | Comparative Example A | Comparative Example 1 | Comparative Example 2 | Comparative Example 3 | Comparative Example 4 | Comparative Example 5 |
|---|---|---|---|---|---|---|---|
| (B) Fiber | Polymer material | None | Fiber H PLA | Fiber B Acrylic resin | Fiber B Acrylic resin | Fiber B Acrylic resin | Fiber I Nylon resin |
| | Fiber diameter (μm) | | 10.0 | 0.6 | 0.6 | 0.6 | 20.0 |
| | Fiber length (μm) | | 50 | 50 | 50 | 50 | 500 |
| | Aspect ratio | | 5.0 | 83.3 | 83.3 | 83.3 | 25.0 |
| | Rate of the number of fibers having a fiber length of 40 μm or more (%) | | 77.3 | 54.3 | 54.3 | 54.3 | — |

| | | | | Comparative Example A | Comparative Example 1 | Comparative Example 2 | Example 3 | Comparative Example 4 | Comparative Example 5 |
|---|---|---|---|---|---|---|---|---|---|
| | Raw material | | | None | PLA | Acrylic resin | Acrylic resin | Acrylic resin | Nylon resin |
| Oil phase | (A) Silicone-based film-forming agent | | Trimethyl siloxysilicate (manufactured by Shin-Etsu Chemical Co., Ltd., Silicone KF-7312J, 50% D5 solution) | 4.00 | 4.00 | 4.00 | 4.00 | 4.00 | 4.00 |
| | (B) Fiber | | Each fiber above | — | 1.00 | 0.02 | 3.00 | 5.00 | 1.00 |
| | (C) Water and nonvolatile oil that is liquid at 20° C. | | Octyl p-methoxycinnamate | 3.00 | 3.00 | 3.00 | 3.00 | 3.00 | 3.00 |
| Water phase | | | Purified water | 20.00 | 20.00 | 20.00 | 20.00 | 20.00 | 20.00 |
| Oil phase | Surfactant | | Polyether-modified silicone (DOWSIL SH3775M FLUID) | 0.40 | 0.40 | 0.40 | 0.40 | 0.40 | 0.40 |
| | | | Dimethylsiloxane/methyl (undecyl glyceryl ether) siloxane copolymer (JP-A-2015-107926, Production example 2) | 0.10 | 0.10 | 0.10 | 0.10 | 0.10 | 0.10 |
| | (E) Volatile oil | | Dimethylpolysiloxane (manufactured by Shin-Etsu Chemical Co., Ltd., Silicone KF-96L-2CS) | 42.00 | 41.00 | 41.98 | 39.00 | 37.00 | 41.00 |
| Water phase | ther component | | Ethanol | 5.00 | 5.00 | 5.00 | 5.00 | 5.00 | 5.00 |
| | | | Magnesium sulfate | 0.50 | 0.50 | 0.50 | 0.50 | 0.50 | 0.50 |
| Powder phase | (D) Powder | (D1) Color pigment | Silicone-treated titanium oxide (manufacture by ISHIHARA SANGYOU KAISHA, LTD., CR-50, average particle diameter: 0.25 μm) | 10.00 | 10.00 | 10.00 | 10.00 | 10.00 | 10.00 |
| | | | Silicone-treated yellow iron oxide | 2.00 | 2.00 | 2.00 | 2.00 | 2.00 | 2.00 |
| | | | Silicone-treated red iron oxide | 0.40 | 0.40 | 0.40 | 0.40 | 0.40 | 0.40 |
| | | | Silicone-treated black iron oxide | 0.20 | 0.20 | 0.20 | 0.20 | 0.20 | 0.20 |
| | | | Silicone-treated fine particle zinc oxide (manufactured by TAYCA Corp. MZY-505M) 25 nm | 3.00 | 3.00 | 3.00 | 3.00 | 3.00 | 3.00 |
| | | Extender pigment | Urethane powder | 3.00 | 3.00 | 3.00 | 3.00 | 3.00 | 3.00 |
| | | | Silicone-coated talc (JA-46R LHC) | 6.40 | 6.40 | 6.40 | 6.40 | 6.40 | 6.40 |

TABLE 2-continued

| | | | | | | | |
|---|---|---|---|---|---|---|---|
| Total amount | | 100.00 | 100.00 | 100.00 | 100.00 | 100.00 | 100.00 |
| (A) Silicone-based film-forming agent | | 2.00 | 2.00 | 2.00 | 2.00 | 2.00 | 2.00 |
| (B) Fiber | | — | 1.00 | 0.02 | 3.00 | 5.00 | 1.00 |
| (C) Water and nonvolatile oil that is liquid at 20° C. | | 23.00 | 23.00 | 23.00 | 23.00 | 23.00 | 23.00 |
| (D) Powder | | 25.00 | 25.00 | 25.00 | 25.00 | 25.00 | 25.00 |
| (E) Volatile oil | | 42.00 | 41.00 | 41.98 | 39.00 | 37.00 | 41.00 |
| Surfactant | | 0.50 | 0.50 | 0.50 | 0.50 | 0.50 | 0.50 |
| (B) (Average fiber diameter)$^2$/fiber content | | — | 100.00 | 18.00 | 0.12 | 0.07 | 400.00 |
| (B)/(A) | | — | 0.50 | 0.01 | 1.50 | 2.50 | 0.50 |
| Evaluation result | Covering effect (the difference ΔL from black artificial leather painted black) | 28.64 | 31.45 | 29.59 | 33.31 | 33.16 | 32.42 |
| | Color development performance (bright color, increased saturation compared to Comparative Example A as reference | 0.00 | 0.63 | 0.07 | 4.43 | 2.65 | 1.78 |
| | Scratch resistance | 11 | 13 | 15 | 3 | 11 | 15 |

TABLE 3

| | | | | Example 10 | Example 11 |
|---|---|---|---|---|---|
| | | | | Fiber B | Fiber B |
| | (B) Fiber | | Polymer material | Acrylic resin | Acrylic resin |
| | | | Fiber diameter (μm) | 0.6 | 0.6 |
| | | | Fiber length (μm) | 50 | 50 |
| | | | Aspect ratio | 83.3 | 83.3 |
| | | | Rate of the number of fibers having a fiber length of 40 μm or more (%) | 54.3 | 54.3 |
| | Raw material | | | Acrylic resin | Acrylic resin |
| Oil phase | (A) Silicone-based film-forming agent | | Trimethyl siloxysilicate (manufactured by Shin-Etsu Chemical Co., Ltd., Silicone KF-7312J, 50% D5 solution) | 4.00 | 4.00 |
| | | | Acrylic silicone dendrimer (manufactured by Dow Toray Co., Ltd., DOWSIL FA 4001 CM, 30% D5 solution) | | 1.00 |
| | (B) Fiber | | Each fiber above | 1.00 | 1.00 |
| | (C) Water and nonvolatile oil that is liquid at 20° C. | | Octyl p-methoxycinnamate | | 2.00 |
| | | | Dimethylpolysiloxane (KF-96L-6CS) | 1.00 | 1.50 |
| | | | Polyisobutene (Parleam EX (pentamer)) | 1.00 | |
| | | | Isononyl isononanoate | 0.50 | 0.50 |
| | | | Diisostearyl malate | 0.50 | |
| Water phase | | | Purified water | 20.00 | 20.00 |
| Oil phase | Surfactant | | Polyether-modified silicone (DOWSIL SH3775M FLUID) | 0.40 | 0.40 |
| | | | Dimethylsiloxane/methyl (undecyl glyceryl ether) siloxane copolymer (JP-A-2015-107926, Production example 2) | 0.10 | 0.10 |
| | (E) Volatile oil | | Dimethylpolysiloxane (manufactured by Shin-Etsu Chemical Co., Ltd., Silicone KF-96L-2CS) | 41.00 | 39.00 |
| Water phase | Other component | | Ethanol (95%) | 5.00 | 5.00 |
| | | | Magnesium sulfate | 0.50 | 0.50 |
| Powder phase | (D) Powder | (D1) Color pigment | Silicone-treated titanium oxide (manufacture by ISHIHARA SANGYOU KAISHA, LTD., CR-50, average particle diameter: 0.25 μm) | 10.00 | 10.00 |
| | | | Silicone-treated yellow iron oxide | 2.00 | 2.00 |
| | | | Silicone-treated red iron oxide | 0.40 | 0.40 |
| | | | Silicone-treated black iron oxide | 0.20 | 0.20 |
| | | | Silicone-treated fine particle zinc oxide (manufactured by TAYCA Corp. MZY-505M) 25 nm | 3.00 | 3.00 |
| | | Extender pigment | Urethane powder | 3.00 | |
| | | | Cellulose powder (manufactured by Daito Kasei Kogyo Co., Ltd., CELLULOBEADS D-5) | | 1.50 |
| | | | Silica (silicic anhydride) (manufactured by JGC Catalysts and Chemicals Ltd., SATINIER M5) | | 1.50 |
| | | | Silicone-coated talc (JA-46R LHC) | 6.40 | 6.40 |
| Total amount | | | | 100.00 | 100.00 |
| (A)Silicone-based film-forming agent | | | | 2.00 | 2.30 |
| (B) Fiber | | | | 1.00 | 1.00 |
| (C) Water and nonvolatile oil that is liquid at 20° C. | | | | 23.00 | 24.00 |
| (D) Powder | | | | 25.00 | 25.00 |
| (E) Volatile oil | | | | 41.00 | 39.00 |
| Surfactant | | | | 0.50 | 0.50 |
| (B) (Average fiber diameter)$^2$/fiber content | | | | 0.36 | 0.36 |
| (B)/(A) | | | | 0.50 | 0.43 |

TABLE 4

| | | | | Example 12 | Example 13 |
|---|---|---|---|---|---|
| | (B) Fiber | | | Fiber B | Fiber B |
| | | | Polymer material | Acrylic resin | Acrylic resin |
| | | | Fiber diameter (μm) | 0.6 | 0.6 |
| | | | Fiber length (μm) | 50 | 50 |
| | | | Aspect ratio | 83.3 | 83.3 |
| | | | Rate of the number of fibers having a fiber length of 40 μm or more (%) | 54.3 | 54.3 |
| | Raw material | | | Acrylic resin | Acrylic resin |
| Oil phase | (A) Silicone-based film-forming agent | | Trimethyl siloxysilicate (manufactured by Shin-Etsu Chemical Co., Ltd., Silicone KF-7312J, 50% D5 solution) | 4.00 | 4.00 |
| | | | Acrylic silicone dendrimer (manufactured by Dow Toray Co., Ltd., DOWSIL FA 4001 CM, 30% D5 solution) | | 1.00 |
| | (B) Fiber | | Each fiber above | 1.00 | 1.00 |
| | (C) Water and nonvolatile oil that is liquid at 20° C. | | Octyl p-methoxycinnamate | 2.00 | 1.00 |
| | | | Dimethylpolysiloxane (KF-96L-6CS) | 4.00 | 4.00 |
| | | | Polyisobutene (Parleam EX (pentamer)) | 2.00 | 1.00 |
| | | | Isononyl isononanoate | 2.00 | 2.00 |
| | | | Diisostearyl malate | 2.00 | 2.00 |
| Water phase | | | Purified water | 25.00 | 31.00 |
| Oil phase | Surfactant | | Polyether-modified silicone (DOWSIL SH3775M FLUID) | 0.40 | 0.40 |
| | | | Dimethylsiloxane/methyl (undecyl glyceryl ether) siloxane copolymer (JP-A-2015-107926, Production example 2) | 0.10 | 0.10 |
| | (E) Volatile oil | | Dimethylpolysiloxane (manufactured by Shin-Etsu Chemical Co., Ltd., Silicone KF-96L-2CS) | 28.00 | 26.00 |
| Water phase | Other component | | Ethanol (95%) | 5.00 | 5.00 |
| | | | Magnesium sulfate | 0.50 | 0.50 |
| Powder phase | (D) Powder | (D1) Color pigment | Silicone-treated titanium oxide (manufacture by ISHIHARA SANGYOU KAISHA, LTD., CR-50, average particle diameter: 0.25 μm) | 10.00 | 7.30 |
| | | | Silicone-treated yellow iron oxide | 2.00 | 1.00 |
| | | | Silicone-treated red iron oxide | 0.40 | 0.20 |
| | | | Silicone-treated black iron oxide | 0.20 | 0.10 |
| | | | Silicone-treated fine particle zinc oxide (manufactured by TAYCA Corp. MZY-505M) 25 nm | 3.00 | 3.00 |
| | | Extender pigment | Urethane powder | 2.00 | |
| | | | Cellulose powder (manufactured by Daito Kasei Kogyo Co., Ltd., CELLULOBEADS D-5) | | 1.50 |
| | | | Silica (silicic anhydride) (manufactured by JGC Catalysts and Chemicals Ltd., SATINIER M5) | | 1.50 |
| | | | Silicone-coated talc (JA-46R LHC) | 6.40 | 6.40 |
| Total amount | | | | 100.00 | 100.00 |
| (A) Silicone-based film-forming agent | | | | 2.00 | 2.30 |
| (B) Fiber | | | | 1.00 | 1.0 |
| (C) Water and nonvolatile oil that is liquid at 20° C. | | | | 37.00 | 41.00 |
| (D) Powder | | | | 24.00 | 21.00 |
| (E) Volatile oil | | | | 28.00 | 26.00 |
| Surfactant | | | | 0.50 | 0.50 |
| (B) (Average fiber diameter)$^2$/fiber content | | | | 0.36 | 0.36 |
| (B)/(A) | | | | 0.50 | 0.43 |

REFERENCE SIGNS LIST

10: electrostatic spraying device
11: syringe
12: high-voltage source
13: conducting collector
**11*a***: cylinder
**11*b***: piston
**11*c***: capillary

The invention claimed is:

1. A film-forming composition for skin, comprising components (A) and (B):

(A) a silicone-based film-forming agent; and (B) a fiber having an average fiber diameter of 0.1 μm or more and 7 μm or less and an aspect ratio (average fiber length/average fiber diameter) of 10 or more and 300 or less in an amount of 0.05 mass % or more and 2 mass % or less relative to the whole film-forming composition, and (C) a liquid material which comprises water and one or more nonvolatile oils that are liquid at 20° C.

wherein a mass ratio of the component (B) to the component (A), (B/A), is 0.05 or more and 1 or less, and a mass ratio of water, (C1), in the component (C) to the component (C), (C1)/(C), is 0.5 or more and 0.90 or less.

2. The film-forming composition for skin according to claim 1, wherein the component (B) is a fiber containing a water-insoluble polymer.

3. The film-forming composition for skin according to claim 1, wherein a content of the component (A) relative to the whole film-forming composition is 0.01 mass % or more and 10 mass % or less.

4. The film-forming composition for skin according to claim 1, further comprising a component (D) powder.

5. The film-forming composition for skin according to claim 1, wherein the component (A) is one or more selected from the group consisting of trimethyl siloxysilicate and acrylic silicone dendrimer.

6. The film-forming composition for skin according to claim 1, wherein said one or more nonvolatile oils is selected from the group consisting of an ester oil, an ether oil, a hydrocarbon oil, a higher alcohol, a fluorine oil, and a nonvolatile silicone oil.

7. The film-forming composition for skin according to claim 1, wherein a mass ratio of water, (C1), in the component (C) to the component (C), (C1)/(C), is 0.6 or more and 0.90 or less.

8. The film-forming composition for skin according to claim 1, wherein a mass ratio of water, (C1), in the component (C) to the component (C), (C1)/(C), is 0.7 or more and 0.90 or less.

9. The film-forming composition for skin according to claim 1, wherein a mass ratio of water, (C1), in the component (C) to the component (C), (C1)/(C), is 0.8 or more and 0.90 or less.

10. A film comprising the film-forming composition for skin according to claim 1.

11. A method for producing a film on a skin surface, comprising applying the film-forming composition for skin according to claim 1 to the skin surface.

12. The method according to claim 11, wherein said one or more nonvolatile oils is selected from the group consisting of an ester oil, an ether oil, a hydrocarbon oil, a higher alcohol, a fluorine oil, and a nonvolatile silicone oil.

13. The method according to claim 11, wherein a mass ratio of water, (C1), in the component (C) to the component (C), (C1)/(C), is 0.6 or more and 0.90 or less.

14. The method according to claim 11, wherein a mass ratio of water, (C1), in the component (C) to the component (C), (C1)/(C), is 0.7 or more and 0.90or less.

15. The method according to claim 11, wherein a mass ratio of water, (C1), in the component (C) to the component (C), (C1)/(C), is 0.8 or more and 0.90 or less.

16. The method according to claim 11, wherein the component (B) is a fiber containing a water-insoluble polymer.

17. The method according to claim 11, wherein a content of the component (A) relative to the whole film-forming composition is 0.01 mass % or more and 10 mass % or less.

18. The method according to claim 11, further comprising a component (D) powder.

* * * * *